(12) United States Patent
Soetaert et al.

(10) Patent No.: US 10,087,491 B2
(45) Date of Patent: Oct. 2, 2018

(54) METHODS, COMPOSITIONS AND DEVICES FOR AMPLIFICATION OF NUCLEIC ACIDS

(71) Applicants: BAYER CROPSCIENCE NV, Diegem (BE); BAYER CROPSCIENCE AG, Monheim am Rhein (DE)

(72) Inventors: Piet Soetaert, Laarne (BE); Martin Leube, Gentbrugge (BE); Bastian Budde, Köln (DE); Klaus Ochmann, Leverkusen (DE); Michael Harnau, Leichlingen (DE)

(73) Assignees: BAYER CROPSCIENCE NV, Diegem (BE); BAYER CROPSCIENCE AG, Monheim am Rhein (DE)

( * ) Notice: Subject to any disclaimer, the term of this patent is extended or adjusted under 35 U.S.C. 154(b) by 30 days.

(21) Appl. No.: 14/437,394

(22) PCT Filed: Oct. 18, 2013

(86) PCT No.: PCT/EP2013/071830
§ 371 (c)(1),
(2) Date: Apr. 21, 2015

(87) PCT Pub. No.: WO2014/064002
PCT Pub. Date: May 1, 2014

(65) Prior Publication Data
US 2015/0267266 A1 Sep. 24, 2015

(30) Foreign Application Priority Data
Oct. 22, 2012 (EP) .................................. 12189381

(51) Int. Cl.
| | | |
|---|---|---|
| *C12Q 1/68* | (2018.01) | |
| *C12Q 1/6895* | (2018.01) | |
| *C12Q 1/6806* | (2018.01) | |
| *B01L 3/00* | (2006.01) | |
| *C12Q 1/6844* | (2018.01) | |
| *C07H 21/02* | (2006.01) | |
| *B01L 7/00* | (2006.01) | |

(52) U.S. Cl.
CPC ............ *C12Q 1/6895* (2013.01); *B01L 3/502* (2013.01); *C12Q 1/6806* (2013.01); *C12Q 1/6844* (2013.01); *B01L 7/52* (2013.01); *B01L 2300/087* (2013.01); *B01L 2300/0816* (2013.01); *B01L 2400/0481* (2013.01); *C12Q 2600/13* (2013.01); *C12Q 2600/158* (2013.01); *C12Q 2600/16* (2013.01)

(58) Field of Classification Search
CPC ............ C12Q 2527/119; C12Q 1/6806; C12Q 1/6844; C12Q 2525/301; C12Q 2527/101; C12Q 2527/125; C12Q 2531/119; C12Q 2565/629; C12Q 1/6895; C12Q 2600/13; C12Q 2600/158; C12Q 2600/16
See application file for complete search history.

(56) References Cited

U.S. PATENT DOCUMENTS

| | | | |
|---|---|---|---|
| 9,568,424 B2 | 2/2017 | Van Haag et al. | |
| 2005/0069887 A1* | 3/2005 | Kitabayashi | C07K 14/195 435/6.12 |
| 2010/0047774 A1 | 2/2010 | Van Haag et al. | |
| 2010/0075311 A1 | 3/2010 | Barrault et al. | |
| 2010/0151531 A1* | 6/2010 | Shikata | C12Q 1/6846 435/91.2 |
| 2017/0100719 A1 | 4/2017 | Van Haag et al. | |

FOREIGN PATENT DOCUMENTS

| | | |
|---|---|---|
| EP | 1026261 A2 | 8/2000 |
| EP | 2077337 A1 | 7/2009 |
| RU | 2435163 C2 | 11/2002 |
| RU | 2432205 C2 | 10/2011 |
| WO | WO 02/088296 A1 | 11/2002 |
| WO | WO 03/048391 A1 | 6/2003 |
| WO | WO 2008/002502 A1 | 1/2008 |

OTHER PUBLICATIONS

Chomczynski et al., "Alkaline Polyethylene glycol-based method for direct PCR from bacteria, eukaryotic tissue samples, and whole blood," Bio Techniques, vol. 40(4), pp. 454-457.
Fang et al., "Loop-Mediated Isothermal Amplification Integrated on Microfluidic Chips for Point-of-Care Quantitative," Anal. Chem., 2010, vol. 82, pp. 3002-2006.
Gill et al., "Nucleic Acid Isothermal Amplification Technologies—A Review," Nucleosides, Nucleotides and Nucleic Acids, vol. 27, 2008, pp. 224-243.
Hwang et al., "A Rapid and Simple Genotyping Method for Various Plants by Direct-PCR," Plant Breed. Biotech. Sep. 2013, vol. 1(3), pp. 290-297.
International Search Report and Written Opinion issued in International Patent Application No. PCT/EP2013/071830 dated Dec. 16, 2013 (13 pages).
Klimyuk et al., "Alkali treatment for rapid preparation of plant material for reliable PCR analysis," The Plant Journal, 1993, vol. 3(3), pp. 493-494.
Lee et al., "Isothermal Amplification of Genetically Modified DNA Sequences Directly from Plant Tissues Lowers the Barriers to High-Throughput and Field-Based Genotyping," J. Agric. Food. Chem., 2009, vol. 57, pp. 9400-9402.

(Continued)

*Primary Examiner* — Teresa E Strzelecka
(74) *Attorney, Agent, or Firm* — Arent Fox LLP

(57) ABSTRACT

Methods, kits and compositions of matter are provided which allow amplification of nucleic acid or interest or DNA of interest, comprising the steps of isolating template nucleic acid or DNA from a biological sample using an alkaline extraction solution and directly adding the extract to a reaction mixture, under conditions to amplify the nucleic acids, wherein the isolated template nucleic acid or DNA in the alkaline extraction solution is not diluted or not neutralized prior to the addition to the reaction mixture.

32 Claims, 7 Drawing Sheets
Specification includes a Sequence Listing.

(56) References Cited

OTHER PUBLICATIONS

Wang et al., "A magnetic bead-based assay for the rapid detection of methicillin-resistant *Staphylococcus aureus* by using microfluidic system with integrated loop-mediated isothermal amplification," Lab Chip, vol. 11, 2011, pp. 1521-1531.

Wang et al., "A simple method of preparing plant samples for PCR," Nucleic Acids Research, 1993, vol. 21(17), pp. 4153-4154.

Wang et al., "Comparison of Three DNA Extraction Methods for Feed Products and Four Amplification Methods for the 5-Junction Fragment of Roundup Ready Soybean," J. of Agriculture and Food Chem., 2012, vol. 60, pp. 4586-4595.

Wu et al., "Integrated Glass Microdevice for Nucleic Acid Purification, Loop-Mediated Isothermal Amplification, and Online Detection," Anal. Chem., 2011, vol. 83, pp. 3336-3342.

Yang et al., "A simple and Rapid Gene Amplification from *Arabidopsis* Leaves Using Any Direct System," J. of Biochemistry and Molecular Biology, vol. 40(3), May 2007, pp. 444-447.

\* cited by examiner

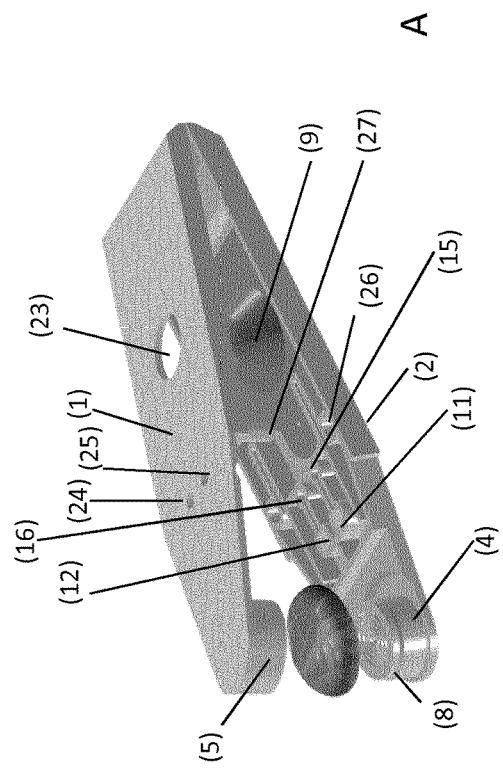
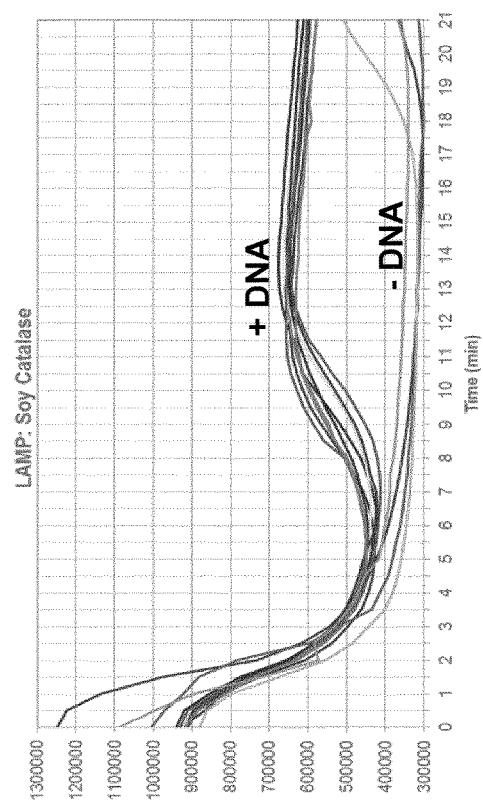
Figure 2

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: F3 oligonucleotide primer

<400> SEQUENCE: 1
gataagttgc tccagactcg                                              20

<210> SEQ ID NO 2
<211> LENGTH: 22
<212> TYPE: DNA
<213> ORGANISM: Artificial Sequence
<220> FEATURE:
<223> OTHER INFORMATION: B3 oligonucleotide primer

<400> SEQUENCE: 2
gcatgacgaa caggatcgta cc                                           22

<210> SEQ ID NO 3
<211> LENGTH: 45
<212> TYPE: DNA

```
<213> ORGANISM: Artificial Sequence
<220> FEATURE:
<223> OTHER INFORMATION: FIP oligonucleotide primer

<400> SEQUENCE: 3
attggctggg agttgcagat agttattctc ctactctgat accca          45

<210> SEQ ID NO 4
<211> LENGTH: 38
<212> TYPE: DNA
<213> ORGANISM: Artificial Sequence
<220> FEATURE:
<223> OTHER INFORMATION: BIP oligonucleotide primer

<400> SEQUENCE: 4
gctcccaagt gtgctcatca atctcctcat ccctgtgc                  38

<210> SEQ ID NO 5
<211> LENGTH: 22
<212> TYPE: DNA
<213> ORGANISM: Artificial Sequence
<220> FEATURE:
<223> OTHER INFORMATION: LoopF oligonucleotide primer

<400> SEQUENCE: 5
agtttggccc aagtctgtgc ct                                   22

<210> SEQ ID NO 6
<211> LENGTH: 22
<212> TYPE: DNA
<213> ORGANISM: Artificial Sequence
<220> FEATURE:
<223> OTHER INFORMATION: LoopR oligonucleotide primer

<400> SEQUENCE: 6
caatcaccac gaaggttta tg                                    22
```

METHODS, COMPOSITIONS AND DEVICES FOR AMPLIFICATION OF NUCLEIC ACIDS

CROSS-REFERENCE TO RELATED APPLICATIONS

This application is the U.S. National Phase of International Application No. PCT/EP2013/071830, filed Oct. 18, 2013, which claims benefit to EP Application No. 12189381.2, filed Oct. 22, 2012.

The current invention relates to the field of nucleic acid amplification, such as nucleic acid amplification to detect the presence of specific nucleic acid sequences in biological samples, such as samples from plants, or plant material or material derived from plants. The methods may be used in a qualitative or quantitative manner, and may also be used to determine whether the concentration of specific nucleic acid sequences in biological samples is below a set threshold level.

Provided are methods and compositions for the amplification of nucleic acids, whereby the nucleic acids, including DNA, are extracted from biological material, or material containing such biological material, using extraction with an alkaline solution, preferably with minimal or even without mechanical maceration of the sample, and whereby the alkaline extract is directly added to a reaction mixture or lyophilized mastermix allowing amplification of the nucleic acid of interest without an intervening additional neutralization or dilution step.

The methods and compositions may be conveniently used together with a single device allowing sampling, preferably of a plant part, and amplification and/or detection of the nucleic acid(s) of interest without the necessity to open the device after sampling the material potentially containing the nucleic acid(s) of interest and/or after the amplification reaction, thereby minimizing the risk of contamination of the sample by any extrinsic nucleic acid.

BACKGROUND ART

In modern agriculture, being able to detect a specific nucleotide sequence of a so-called nucleic acid of interest or target sequence, is becoming more and more important. This capability allows e.g. to rapidly detect specific nucleic acid sequences associated with the presence of a particular characteristic or trait in a plant, thereby allowing to develop particular plants with particular combinations of characteristics in a more direct and more efficient manner. Such capability also allows to detect particular variant alleles in plants.

With the development of transgenic plants, a need has arisen to be able to detect the presence of biological material comprising particular transgenic events, e.g. in the field, in the variety development of plants, or in the commercial chain (grain production, grain transport, grain storage etc.), preferably at higher speed, lower cost and with greater versatility. Moreover, different transgenic events may comprise similar or even identical nucleic acids, and often it is desirable to be able to distinguish between such different transgenic events, comprising similar or identical nucleic acids, requiring the application of event specific detection methods and tools.

Additionally, more and more plant diseases can be rapidly and unambiguously diagnosed via detection of specific nucleotide sequences, associated with the pathogens (fungal, viral, bacterial, nematode or other plant pests) causing the disease.

The applicability of detection of specific nucleotide sequence in biological material is of course not limited to agricultural applications, but also extends into other fields, including the medical field, forensics, genetic counseling etc.

Various detection methods are based upon amplification of a target nucleic acid and/or DNA having a specific nucleotide sequence, the oldest process being the polymerase chain reaction.

Of particular interest are the isothermal DNA amplification methods, including the so-called LAMP or Loop-mediated Isothermal Amplification as described in e.g. U.S. Pat. No. 641,027 (Eiken) The method is characterized by the use of 4 different primers specifically designed to recognize 6 distinct regions on the target gene and the reaction process proceeds at a constant temperature using strand displacement reaction. Amplification and detection of target nucleic acid of interest can be completed in a single step, by incubating the mixture of the biological sample or a nucleic acid extract thereof, primers, DNA polymerase with strand displacement activity and substrates at a constant temperature (about 65° C.). It provides high amplification efficiency, with DNA being amplified 109-1010 times in 15-60 minutes. Because of its high specificity, the presence of amplified product can indicate the presence of target gene (http://loopamp.eiken.co.jp/e/lamp/index.html).

Other isothermal DNA amplification methods include the so-called Nicking Enzyme Amplification Reaction (NEAR) (Envirologix). NEAR uses a nicking enzyme and strand-displacing polymerase to generate small pieces of DNA that feed a DNA extension reaction; alternating cycles of nicking and extension lead to exponential amplification. The method is described in e.g. US 2009/0017453.

Yet another isothermal nucleic acid and/or DNA amplification method is the so-called Recombinase Polymerase Amplification (RPA) (TwistDx). The RPA method uses recombinases, which are capable of pairing oligonucleotide primers with homologous sequence in duplex DNA. Through this method, DNA synthesis by a DNA polymerase is directed to defined points in a sample DNA. If the target sequence is present, a DNA amplification reaction is initiated. Recombinase polymerase amplification is described e.g. in U.S. Pat. No. 7,270,981.

Other isothermal amplification methods are described in Gill and Ghaemi, 2008, Nucleosides Nucleotides Nucleic Acids, 27(3) 224-243.

An important step in all nucleic acid and/or DNA amplification methods is the preparation of the template nucleic acids from the biological material. For automatic processing of the amplification reaction, convenient and efficient nucleic acid extraction from the biological samples, yielding sufficient template nucleic acids, and preferably in a solution without turbidity, is preferred. Preferably, the extraction step should only have minimal maceration, or even avoid mechanical maceration of the biological material as this may introduce turbidity in the solution. Alkaline extraction of template nucleic acid and/or DNA from biological samples may provide such a method using only minimal maceration of the biological sample.

Klimyuk (1993) (Plant Journal 3(3) 493-494) described alkali treatment for rapid preparation of plant material for reliable PCR analysis.

Chomczynski and Rymaszewski (2006) described and alkaline polyethylene glycol-based method for direct PCR from bacteria, eukaryotic tissue samples, and whole blood. (BioTechniques, 40, 454-457).

A drawback of the alkaline extraction methods, is that the resulting extract needs to be neutralized or diluted sufficiently, prior to adding the extract or an aliquot thereof to the amplification reaction mixture. Such a dilution or neutralization step results in additional handling of the sample, increasing the risk of contamination of the sample with unwanted nucleic acids and/or DNA. The additional step further complicates automated processing of the amplification reaction (see also Lee et al., 2009, J. Agric. Food Chem. 2009, 57, 9400-9402).

Furthermore, there is a need for automated processing of sampling, amplification and detection with a minimum of process steps. Such kits and/or devices for automated processing could be used in environment outside of a laboratory, particularly if the chemistry and processing is robust.

Current detection methods to be used outside of a laboratory environment are protein based detection tools, such as Lateral Flow Strips. Protein based detection tools fail to detect e.g. transgenic plants with silenced genes causing a trait, temporal or special expression of proteins, or cannot distinguish between different plants or transgenic events expressing the same or similar proteins.

The current invention provides a solution to these problems as described hereinafter in the summary, detailed embodiments, examples, drawings and claims.

SUMMARY OF THE INVENTION

In one embodiment of the invention, a composition of matter suitable for the amplification of nucleic acids is provided comprising a mixture of deoxynucleotides (dNTPs), divalent cations, such as provided by $Mg_2SO_4$ or other magnesium salts, an enzyme capable of DNA amplification, and primers suitable to amplify a target nucleic acid, such as a DNA of interest, characterized in that the mixture further comprises a salt containing ammonium as cation and an anion of a weak acid, such as ammoniumpentaborate ($NH_4B_5O_8$), preferably in a final concentration of between 10 mM and 100 mM, preferably between 30 mM and 40 mM, and further an organic acid, preferably a dicarboxylic acid which may be selected from oxalic acid, malonic acid, succinic acid, glutaric acid, adipic acid, pimelic acid, suberic acid, azelaic acid, sebacic acid, glucuronic acid, lactic acid, tartaric acid, fumaric acid, maleic acid or a mixture thereof, preferably malic acid, preferably in a final concentration of between 10 mM and 40 mM, preferably 40 mM. The divalent cations may be provided by $Mg_2SO_4$ and may have a final concentration of between 1-10 mM, preferably between 4-8 mM. and the dNTPS may have a final concentration of between 0,2 mM to 1,4 mM, preferably 0.4 mM to 0.9 mM. The enzyme capable of DNA amplification may be selected from DNA I polymerase, Klenow polymerase, TaqI polymerase, a DNA polymerase with strand displacing properties, phi 29 polymerase, Bst polymerase, Csa polymerase, 96-7 polymerase, Bsm polymerase or GspSSD polymerase.

In another embodiment of the invention, the composition suitable for the amplification of nucleic acids may further comprise molecules allowing fluorescent detection of amplified nucleic acid or DNA, such as dimeric dyes comprising monomeric dyes linked by a neutral molecule, which become fluorescent only when bound to nucleic acid or intercalating dyes including N',N'-dimethyl-N-[4-[(E)-(3-methyl-1,3-benzothiazol-2-ylidene)methyl]-1-phenylquinolin-1-ium-2-yl]-N-propylpropane-1,3-diamine) or fluorescent dye SYTO-81 (Invitrogen).

In yet another embodiment of the invention, the composition suitable for the amplification of nucleic acids may further comprise molecules allowing detection of amplified nucleic acid, via antibody specific binding or via affinity binding, or via nucleic acid based hybridization assays or combinations thereof (also known as Lateral Flow Strip assays).

In still another embodiment of the invention, the composition suitable for the amplification of nucleic acids may further comprise a detergent, preferably Triton X-100, or Tween 20 or Pluronic F-68, preferably in a concentration of between 0.01% and 0.5%, preferably about 0.1%.

Also provided are compositions suitable for the amplification of nucleic acids further comprising a lyophilization protection agent, such as trehalose, which may be present in a final concentration of between 0.001 to about 5% and/or betaine in a concentration of between 0.05 mM to 1 M.

In all embodiments of the invention, the composition suitable for the amplification of nucleic acid is suitable to amplify a nucleic acid and/or DNA sequence of interest in a biological sample, such as a biological sample derived from a plant of interest. The nucleic acid or DNA sequence of interest may be specific for a commercially available transformation event, or for a experimentally available transformation event. The nucleic acid or DNA sequence of interest may also be specific for the presence of a specific allele, such as a variant allele, or the nucleic acid or DNA sequence may be a marker, such as a QTL marker. Concentrations of primer oligonucleotides are as known in the art for the different nucleic acid amplification methods.

In another embodiment of the invention, the composition suitable for the amplification of nucleic acids as herein described may be subjected to lyophilization.

In yet another embodiment of the invention, a kit comprising the composition suitable for the amplification of nucleic acids as herein described is provided.

The kit may be comprised within a device, said device comprising
  a. a means for sampling of the biological material;
  b. a liquid reservoir comprising an alkaline extraction solution;
  c. appropriate channels to direct the alkaline extraction solution, upon activation, over the biological sample into the reaction mixture; and
  d. optionally a means to detect amplification of nucleic acids.

The kit may also be comprised within a cartridge, said cartridge comprising
  a) a first component, preferably a base component, preferably covered on both sides with transparent coats, thereby forming channels and chambers (1) and a second component, preferably a cover component (2), fitting together to be closed, preferably by aligning one structure onto the other, preferably around a hinge section (3);
  b) said first and second or said base and cover components containing fitting and corresponding chamber parts (4) and (5) which when the first and second component or base and cover component are aligned form a chamber A, fit to receive the biological sample; wherein the chamber A is preferably water-tight;
  c) said first or said base component further comprising attached to it, a liquid reservoir (9) containing an alkaline solution; said liquid reservoir being connected to chamber A via a channel (10);
  d) said first or said base component further containing at least one, preferably two chambers B (11) (12) connected to said chamber A or said base chamber A part (4) by at least one channel (13);

e) said first or said base component further containing at least one, preferably two chambers C (15) (16), each connected to said at least one chamber B by a channel (17) (18);

f) said first component or said base component, further optionally containing at least one, preferably two chambers D (19)(20), each connected to said at least one chamber C by a channel (21) (22);

g) said second component or said cover component preferably containing a physical access (23), preferably a hole, to allow interaction with the liquid reservoir (9);

h) said second or cover component further optionally containing at least one, preferably two optically transparent region(s) over the region of said chamber B or said two chambers C allowing monitoring of the chamber B or C (24) (25);

wherein said composition of matter is contained within said chambers B.

The invention also provides a method for amplifying nucleic acid or DNA of interest comprising using a composition suitable for the amplification of nucleic acids as herein described or a kit as herein described. The method is preferably an isothermal, DNA amplification process. The template nucleic acid or DNA may be provided in an alkaline solution and may further comprise carrier DNA.

The invention also provides a method for amplification of nucleic acid or DNA, comprising the steps of a) isolating template nucleic acid or DNA from a biological sample, such as a plant part, organ or tissue, a portion of a plant leaf, seed or seed powder, using an alkaline extraction solution, such as an alkaline extraction solution containing KOH, NaOH or LiOH, preferably KOH, preferably in a concentration of 25 mM to 100 mM, particularly in a concentration of about 50 mM, and preferably processing the biological sample with minimal or even without mechanical maceration and b) providing ingredients and conditions to amplify the nucleic acid or DNA wherein said isolated template nucleic acid or DNA in said alkaline extraction solution is not diluted or not neutralized prior to said step b), but rather directly added to the reaction mixture or lyophilized mastermix.

BRIEF DESCRIPTION OF THE DRAWINGS

FIG. 2: Panel A: Three-dimensional representation of a cartridge according to the invention. For reference numbers, see FIG. 1. Panel B: sampling of a plant leaf using the cartridge according to the invention. Panel C: Real-time fluorescence detection after the reaction has been activated through actuation of the fluid blister, thereby forcing the nucleic acid or DNA extraction buffer over the leaf sample, reconstituting the lyophilized reaction mixture. The cartridge was heated to a constant temperature of 65° C.

DETAILED DESCRIPTION OF VARIOUS EMBODIMENTS OF THE INVENTION

Figure 1A:
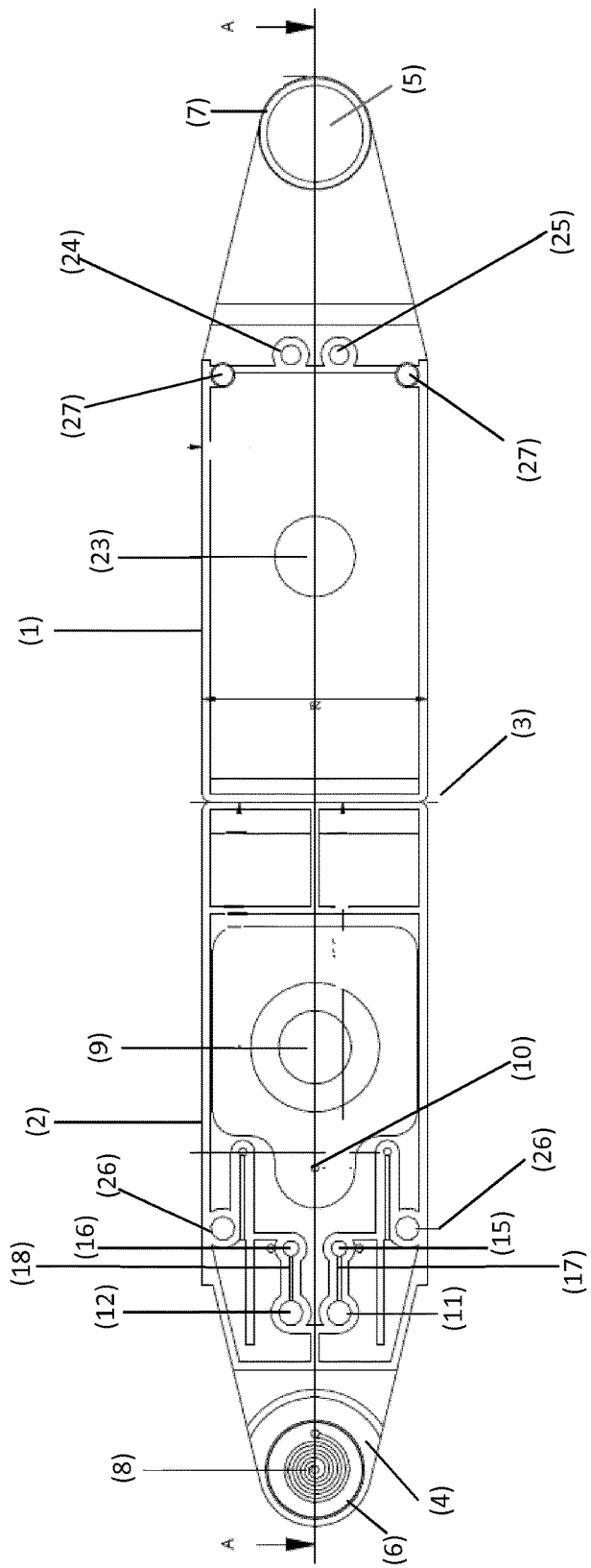
FIG. 1: Schematic drawing of an unfolded cartridge as described in this application. Panel A: view of the inner side of the unfolded cartridge. Panel B: view of the outer side of the unfolded cartridge. Panel C: cross section A-A of the unfolded cartridge. (1) upper support or cover; (2) lower support or cover; (3) hinge section; (4) lower part of chamber A; (5) upper part of chamber A; (6) (7) protruding parts or clips of the chamber A parts; (8) a fluid transporting channel for distribution of the fluid over the biological sample; (9) liquid reservoir for the alkaline extraction solution; (10) fluid channel; (11) (12) chambers B which may comprise the lyophilized reaction mixture; (13) fluid channel; (14) T-form junction; (15) (16) chambers C; (17) (18) fluid channels; (19)(20) chambers D; (21) (22) fluid channels; (23) hole in the upper cover allowing to apply pressure to the liquid reservoir; (24) (25) optically transparent regions; (26) holes and (27) protrusions in the cover for locking the upper and lower support together.

The current invention is based on the optimization of nucleic acid amplification reaction conditions, allowing direct enzymatic nucleic acid amplification using as template, nucleic acid and/or DNA extracted from biological material by means of an alkaline solution, without any intervening neutralization or dilution step as in the prior art. The direct addition of nucleic acid and/or DNA also avoids the need for temperature based denaturation of the nucleic acid to allow primer binding, and may thus contribute to the efficiency of detecting the nucleic acid of interest.

Thus, in one embodiment of the invention, a method is described for amplification of nucleic acids such as DNA, comprising the steps of a. isolating template nucleic acid or DNA from a biological sample using an alkaline extraction solution b. providing ingredients and conditions to amplify DNA wherein said isolated template DNA in said alkaline extraction solution is not diluted or not neutralized prior to said step b) but rather directly added to those ingredients.

The alkaline extraction solution may comprise KOH, NaOH or LiOH, preferably KOH, preferably in a concentration range of about 25 to 100 mM, particularly in a concentration range of about 50 mM. One of the advantages of alkaline extraction of nucleic acid and/or DNA from biological samples is that there is no need to process the biological sample by mechanical maceration, thereby avoiding introduction of turbidity in the extracts or subsequent reaction mixtures. Of course a certain level of maceration may be acceptable or even preferable. E.g. clipping of a leaf sample already introduces a minimal level of maceration to the sample, although no further maceration may be required. Further minimal maceration may include punctuation of the sample or squeezing the sample.

Preferably, the extraction solution also comprises carrier DNA, i.e. DNA which does not contain the nucleic acid of interest, and preferably is obtained from an organism unrelated to the sampled biological material. For plant material, a convenient source of carrier DNA is fish sperm DNA, although DNA from any other source may also be used. The presence of the carrier DNA reduces the frequency of false positives in the subsequent amplification and detection of amplified DNA.

To allow direct addition of alkaline extract containing the template nucleic acid or template DNA to the reaction mixture, the reaction mixture has a composition having a sufficient buffering capacity, yet without increasing the ionic strength of the reaction mixture too high, so that the amplification enzyme is not inhibited.

To allow direct amplification without extra neutralization or dilution step, the invention provides in one embodiment a composition of matter suitable for the amplification of nucleic acid molecules and/or DNA comprising a mixture of divalent cations, deoxynucleotides (dNTPs), an enzyme capable of DNA amplification, and primers suitable to amplify a nucleic acid and/or DNA of interest, characterized in that the mixture has a buffering capacity at a sufficiently low ionic strength to sufficiently neutralize an alkaline solution containing template nucleic acid or DNA in order to allow the amplification enzyme to function. Such composition may e.g. comprise a salt containing ammonium as cation and an anion of a weak acid, and/or a further organic acid, preferably a dicarboylic acid.

As used herein, a weak acid is an acid which has a pKa of about 2 to 6. In one embodiment the salt is ammoniumpentaborate ($NH_4B_5O_8$). In another embodiment, the salt may be a salt of a weak acid and ammonium as cation, whereby upon solution in water the achieved pH is around the optimum pH of the enzyme to be used in the amplification reaction. In a preferred embodiment, the pH after solution of the ammonium salt is around 8.5.

The ammoniumpentaborate in the reaction mixture may have a final concentration of between 10 mM and 100 mM, preferably between 30 and 40 mM, particularly about 30 mM. The ammonium cation and borate anion may also be obtained from other sources. E.g. the ammonium cation can be obtained from ammoniumsulfate and the borate anion from Tris-borate. However, care has to be taken to keep the total ionic strength of the buffer low enough to avoid inhibition of the polymerase enzyme.

The additional organic acid may be selected from oxalic acid, malonic acid, succinic acid, glutaric acid, adipic acid, pimelic acid, suberic acid, azelaic acid, sebacic acid, glucuronic acid, lactic acid, tartaric acid, fumaric acid, maleic acid or a mixture thereof, preferably in a final concentration of between 10 and 40 mM, preferably about 40 mM. It is important that the organic acid is not inhibitory to the amplification reaction or the amplification. It has e.g. been found that citric acid or ascorbic acid can be inhibitory for a LAMP reaction.

Another important constituent of the reaction mix for amplification of nucleic acids and/or DNA are the oligonucleotide primers. The term "primer" as used herein encompasses any nucleic acid, preferably a DNA, that is capable of priming the synthesis of a nascent nucleic acid in a template-dependent process, such as PCR, NEAR, RPA, LAMP. Typically, primers are oligonucleotides from 10 to 30 nucleotides, but longer sequences can be employed. Primers suitable for LAMP may be up to 60 nucleotides. Primers may be provided in double-stranded form, though the single-stranded form is preferred. The primers recognize specifically the target nucleotide sequence of the nucleic acid of interest, and specifically hybridize to that nucleic acid, thereby determining the specificity of the assay with regard to the nucleic acid of interest to be amplified/detected. Primers may contain further chemical modifications allowing detection of the amplified nucleic acid or DNA as described herein after. The exact arrangement and structure of the primers is also arranged by the amplification method to be used. For LAMP e.g. 4 types of primers are designed, based on 6 distinct regions of the target gene: the F3c, F2c and F1c regions at the 3' side and the B1, B2 and B3 regions at the 5' side:

FIP: Forward Inner Primer (FIP) consists of the F2 region (at the 3' end) that is complementary to the F2c region, and the same sequence as the F1c region at the 5' end.

F3 Primer: Forward Outer Primer consists of the F3 region that is complementary to the F3c region.

BIP: Backward Inner Primer (BIP) consists of the B2 region (at the 3' end) that is complementary to the B2c region, and the same sequence as the B1c region at the 5' end.

B3 Primer: Backward Outer Primer consists of the B3 region that is complementary to the B3c region.

The reaction may further be optimized by inclusion of so-called Loop Primers (either Loop Primer B or Loop Primer F), containing sequences complementary to the single stranded loop region (either between the B1 and B2 regions, or between the F1 and F2 regions) on the 5' end of the dumbbell-like structure, provide an increased number of starting points for DNA synthesis for the LAMP method (see also loopamp.eiken.co.jp/e/lamp).

Yet another important constituent of the reaction mix for amplification of nucleic acids and/or DNA are the enzymes for amplification. Depending on the method used these enzymes include DNA I polymerase, Klenow polymerase, TaqI polymerase, a DNA polymerase with strand displacing properties, phi 29 polymerase, Bst polymerase (NEB), Csa polymerase, 96-7 polymerase (http://www.nippongene.com), Bsm polymerase (Fermentas), GspSSD polymerase (Optigene) and others.

In one embodiment of the methods of the invention, the composition is suitable for use in connection with the so-called LAMP method as herein described. However the compositions and methods may also be used in other types of amplification including RPA, PCR, NEAR etc.

Other constituents in the reaction mixture are considered less critical and comprise dNTPS in a final concentration of between 0.2 mM to 1.4 mM; and divalent cations ($Mg^{2+}$, $Mn^{2+}$, . . . ) in a final concentration of between 1-10 mM. $Mg_2SO_4$ is a suitable salt, but may be replaced with other salts.

Detection of the amplified nucleic acid of interest, preferably DNA of interest, can be performed in any way known in the art. The detection may be specific or aspecific or a mixture of both. The detection could be based on a colorimetric, turbidimetric, luminescent or fluorescent assay. Fluorescent detection is considered to be very convenient. In general, fluorescent nucleic acid detection is achieved using fluorescent nucleic acid dyes which can be classified in two major classes: intercalators and minor groove binders, although there are other dyes that may bind to nucleic acids via multiple modes, including electrostatic interaction between a positively charged dye and the negatively charged nucleic acid. Fluorescent intercalators are dyes that bind to double stranded DNA or double stranded RNA by inserting themselves in between a neighbouring base pair. Minor groove-binders are dyes that bind to the minor groove of double stranded DNA.

Intercalator dyes include ethidium bromide (well known in the art, but less preferred due to its mutagenic or carcinogenic properties) or asymmetric cyanine dyes such as SYBR Green I, SYBR Gold or SYBR safe. SYBR Green is N',N'-dimethyl-N-[4-[(E)-(3-methyl-1,3-benzothiazol-2-ylidene)methyl]-1-phenylquinolin-1-ium-2-yl]-N-propylpropane-1,3-diamine). SYBR Safe has been described in US patent application publication No. 2005/0239096 (herein incorporated by reference).

US patent application publication No 2006/0211029 (hereby incorporated by reference) describes several dimeric fluorescent dyes including EVA Green. Dimeric fluorescent dyes comprise two monomeric dyes and a suitable linker to form a dimeric dye, whereby in the absence of nucleic acids, the dimeric dye assumes a hairpin-like conformation which has a low or no background level fluorescence. In the presence of nucleic acids, the dye assumes an open random conformation, which allows the dye to interact with the nucleic acid and increase the fluorescence.

Another fluorescent dye which could be useful is SYTO-81 (Invitrogen).

Tanner et al. (2012, Biotechniques 53, 2) describe fluorescent probes for LAMP reaction which when used with similar primers on pure DNA results in detection of amplification which appears to be slightly later but with a significantly better signal/noise ration than when using e.g. SYBR Green.

Detection of the amplified nucleic acid of interest may also occur via antibody specific recognition. To this end, the amplified nucleic acid of interest may include modifications incorporating specific antigens recognized by a specific antibody, which may be introduced e.g. by modification of the oligonucleotide primers used for the nucleic acid amplification. Detection could also be achieved by affinity based assays (using e.g. streptavidin-biotin) or hybridization based assays. Use of this type of assays is well known in the art (e.g. Lateral Flow Strips).

As used herein, a biological sample is used to indicate any biological material, particularly biological material comprising nucleic acids, or material containing or derived from such biological material, provided that nucleic acids can still be detected. A non-limiting list of biological material includes leaf segments, stem segments, root segments, seed, seed powder, meal, fibers, single seeds, seed chips, seed bulks etc. Biological material may comprise or be obtained from fungi, bacteria, including rhizobacteria, viruses, plants, animals, Protista and the like.

The compositions for the amplification of a nucleic acid of interest as herein described may further comprise detergents such as Triton X-100, Tween 20, Pluronic-F-68(Invitrogen), or combinations thereof preferably in a concentration of about 0.1%.

Conveniently, the compositions for the amplification of a nucleic acid of interest as herein described are provided in a lyophilized form. To this end, the compositions are supplemented with lyophilization protection agents, such as trehalose, preferably in a final concentration of 0.001% to about 5%. Preferably, the components are lyophilized on a solid or semi-solid support or scaffold ("pad"), allowing for easy handling.

The compositions of matter and methods for the amplification of a nucleic acid of interest, may be used in a device or cartridge allowing sampling of biological material, nucleic acid or DNA extraction and amplification and detection without a further need for opening the device after the sampling or amplification has taken place. Nevertheless, it may be advantageous in certain embodiments to be able to open the device or cartridge during the processing, particularly after the amplification reaction has taken place, e.g. to allow a particular form of detection.

Such a device may comprise
a. a means for sampling of the biological material;
b. a liquid reservoir comprising an alkaline extraction solution;
c. a reaction mixture, i.e. composition of matter as herein described;
d. appropriate channels to direct the alkaline extraction solution, upon activation, over the biological sample to the reaction mixture;
e. optionally a means to detect amplification of nucleic acids.

Figure 1B:
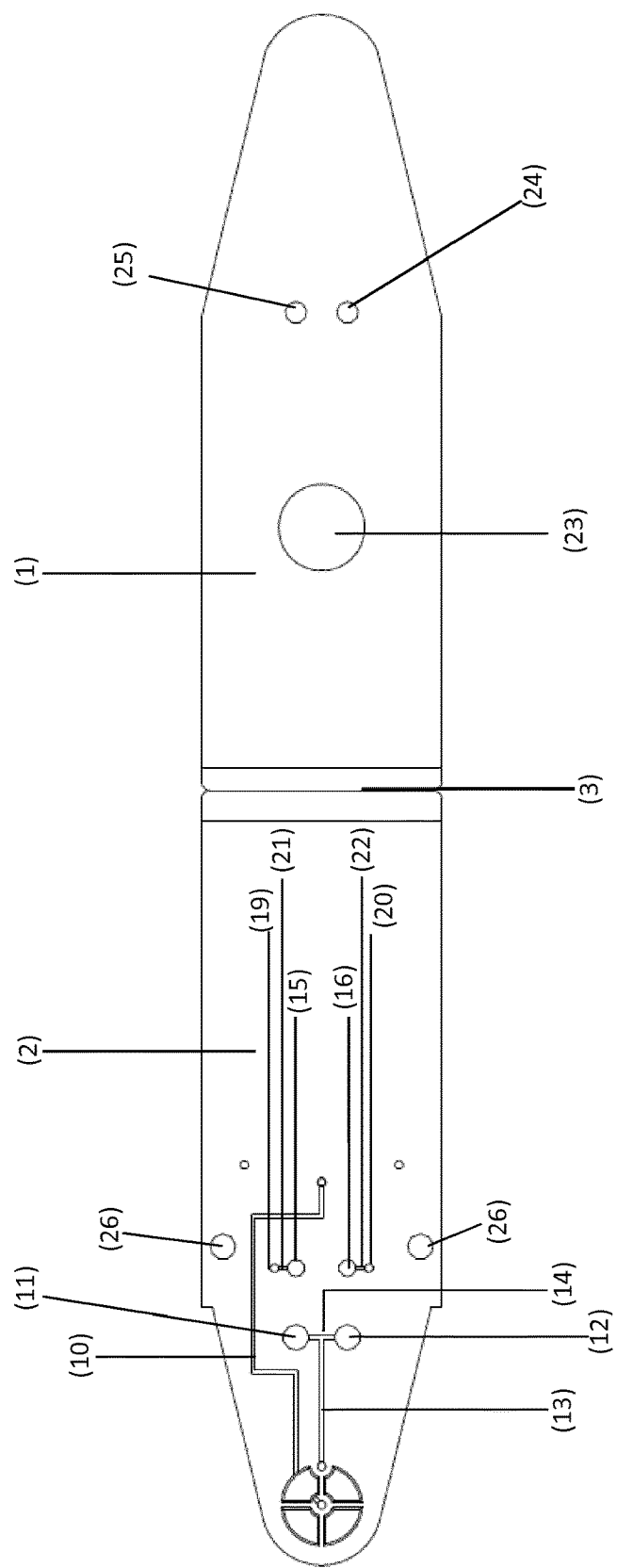
Figure 1C:
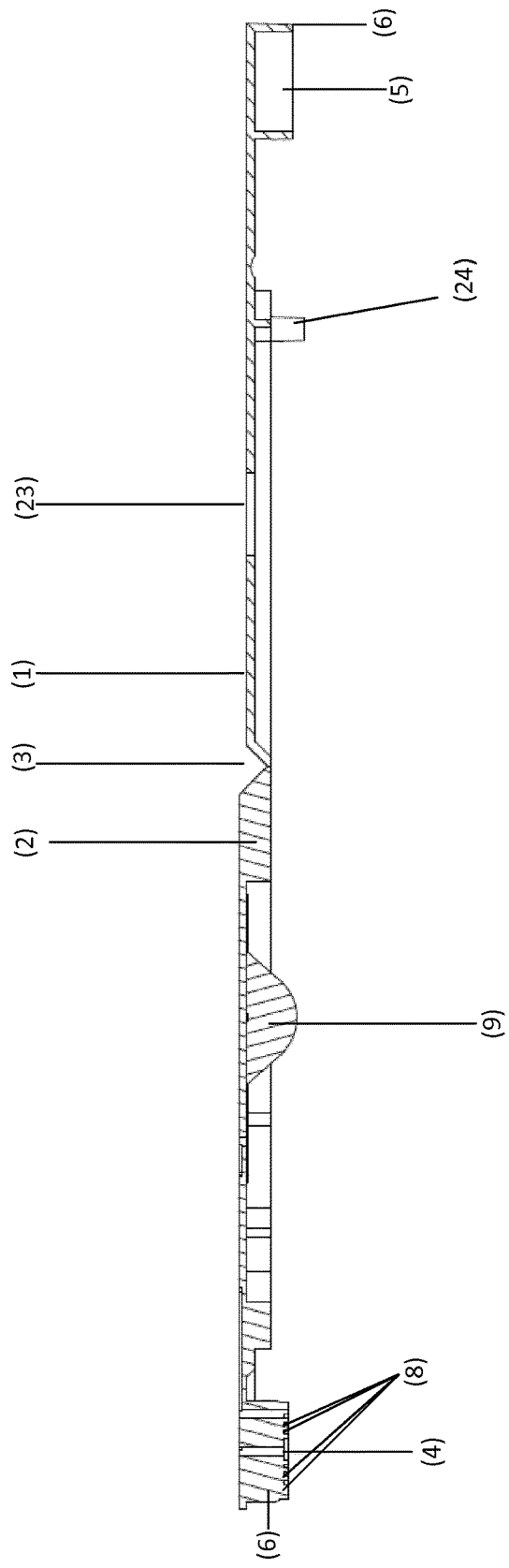

One embodiment of such device is schematically represented in FIGS. 1 a to c. The device may comprise:

An cover (1) and base (2) component fitting together to be closed, preferably by aligning one structure onto the other, preferably around the hinge section (3).

The base and upper component containing fitting and corresponding chamber parts (4) and (5) which when the base and upper component are aligned, e.g. are folded together, form a chamber A, fit to receive the biological sample, whereby optionally the protruding parts or clips of the sample chamber parts (6) and (7) can be used to separate the biological sample, such as a leaf part, from surrounding biological material. Preferably, the chamber A is water-tight.

The chamber A may further comprise a fluid transporting channel (8), such as a channel in the form of spiral, optionally having several openings allowing optimal distribution of the extraction buffer over the biological sample.

Attached to one of the components is a liquid reservoir (9) containing an alkaline extraction solution. The liquid reservoir may be a burst buffer chamber, such as a blister described in WO2010/094249; WO2011/006460 or WO2009/071078. The liquid reservoir is connected through the chamber A via a channel (10).

The upper or base component, preferably the base component, further contain at least one, preferably two chambers B (11) (12) connected to at least one part of chamber A, preferably the lower chamber A part (4) by a channel (13), said chambers allowing to receive a composition of matter as herein described for the amplification of nucleic acids of interest. Preferably, when two chambers B are present, one of the chambers is used to receive a composition of matter suitable for the detection of a nucleic acid of interest, whereas the other chamber is used to receive a composition of matter suitable for the detection of a nucleic acid of interest known to be present in the biological sample (such as an endogenous gene of the sampled plant), thereby acting as positive control for the functioning of the amplification reaction. The composition of matter suitable for the detection of a nucleic acid of interest may be provided in the form of a lyophilized composition of matter, preferably in the form of a pad comprising the lyophilized composition of matter. This also provides for interchangeability of the amplification reactions which can be performed using different pads comprising different compositions of matter as herein described, thereby increasing the versatility of the device. When two chambers B are present, the channel connecting the sample chamber to the reconstitution chambers needs to allow the distribution of the extraction buffer containing the extracted template DNA over the two reconstitution chambers, preferably in equal portions. This can be achieved using a channel with a T-form junction (14).

The base and cover component, preferably the base component, further contain at least one, preferably two chambers C (15) (16), connected to the at least one chamber B by a channel (17) (18). When two chambers C are present, each chamber C is preferably connected by a channel to one chamber B only.

The base and cover component, preferably the base component, further optionally contain at least one, preferably two chambers D (19)(20) connected to the at least one chamber C by a channel (21) (22). When two chambers D are present, each chamber C is preferably connected by a channel to one chamber C only.

The base and cover component preferably contains a means allowing physical access (such as a hole) (23) to allow interaction with the liquid reservoir (9).

The base and cover component further optionally contains an at least one, preferably two optically transparent region over the region of said chamber B or said chamber(s) C allowing (optionally fluorescent or colorimetric) detection (24) (25).

The channels may further contain one or more valve systems, such as e.g. the valve systems described in WO2012/048685 to direct the flow of the liquid in the channels in one direction.

Optionally, the base and cover components may contain means for locking the upper and lower support together, such as holes (26) and protrusions (27) in the cover.

As used herein "a pad" is a thin inert support material, such as siliconized rock wool, or polymer fleece or fiber, comprising the composition of matter for amplification of nucleic acids as herein described. The composition of matter may be contained in two inert supports, or may applied to one inert support only. Preferably, the composition of matter has been lyophilized. The inert support should allow the buffer fluid to pass. Preferably, the inert support tightly fits into a cartridge chamber, thereby additionally functioning as a sieve for retention of particles interfering with the reaction and/or detection.

The cartridge may be filled with biological material. This can be achieved by clipping the first and second, or upper (1) and lower (2) supports or covers together, thereby fitting the first and second or lower (4) and upper (5) chamber parts together in such a way that the biological material is entrapped in the closed chamber A, which may thus serve as a sample chamber. E.g the cover may be slipped over a plant leaf, so that upon closing the sample chamber edges clip out a piece of leaf, enclosed in the chamber A. Alternatively, seed or seed powder or other material containing or derived from biological material potentially comprising the nucleic acids of interest may be deposited in the lower sample chamber half, and the upper cover can be folded and closed over the biological material.

Subsequently, the alkaline extraction solution contained in the liquid reservoir (9) is directed through the channel connecting the liquid reservoir and the chamber A (10). This may be achieved by applying pressure to the liquid reservoir (9). The alkaline solution passes over the biological material in the chamber A (4) (5), optionally through the distribution device (8) thereby extracting nucleic acids, such as DNA, present in the biological sample.

The extraction fluid containing nucleic acids from the biological sample is guided through the channel (13) connecting the chamber A and the chamber(s) B (15) (16). Equal distribution of the extraction fluid over the chambers B may be ensured by a T-form junction (14) in the channel.

In the chamber(s) B, the alkaline extraction solution containing the extracted nucleic acids and/or DNA passes over and through the pads containing a composition of matter for amplification of nucleic acids according to the invention. In this step of the reaction, the extraction fluid may be filtered going through the pads, and is mixed with the composition of matter for amplification of nucleic acids, reconstituting a reaction mixture, which is guided towards the chamber(s) C (21) (22) through the channels connecting chamber(s) B and chamber(s) C (17) (18).

The cartridge is then subjected to a temperature regime required for the amplification of nucleic acids suitable for the reaction mix used. When isothermal amplification is used, the cartridge may be heated for a period of time to a constant temperature, such as e.g. 65° C. Usually, the reaction will be allowed to progress for a period of time of about 5 to 60 minutes, or 20 to 30 minutes. The heating may also be applied additionally during the nucleic acid extraction step, prior to the amplification step.

Amplification of the nucleic acid of interest (or of the control nucleic acid) may be monitored through the region allowing optical monitoring of the chamber(s) C (24) (25). This monitoring or detection may either be performed continuously as the amplification reaction progresses (real-time) or may be performed only at the end of the reaction (end-point detection). The detection may also occur via an affinity or antibody based detection unit or hybridization based assay, which may be built-in, or plugged in after the amplification reaction has taken place.

The chamber(s) D (19) (20) may function as a waste chamber and allow to capture any expansion of the fluid during heating. Return flow of liquid through the channels may be prevented by providing passive valves in the channels.

In one embodiment of the invention, the base and/or cover component may be cast as a single piece, whereby the channels are cast into the molded component. In an alternative embodiment the base and cover component may be produced by milling the channels into the material of the base and upper component, whereby the base and upper component are covered by transparent cover foil. In a preferred embodiment the cartridge is molded from chemically inert material, preferably with low binding affinity for nucleic acid. The cartridge may be molded from polypropylene.

The optimization of the composition of matter for amplifying nucleic acids to allow amplification without a preceding neutralization step after extraction of nucleic acids or DNA from biological material by an alkaline solution, allowed to design a cartridge comprising only one buffer contained in one liquid reservoir. The design of the cartridge with only one liquid reservoir provides the additional advantage that cartridges may be produced which are simpler to use and cheaper to produce.

The cartridge may be put into a device allowing actuation by pressure, preferably controlled actuation by controlled pressure of the liquid reservoir. The device may also allow heating of the cartridge up to the required temperature. Furthermore the device may allow real-time or end-point monitoring of the detection of the amplified nucleic acids of interest. In one embodiment of the invention, the device accepting the cartridge may be hand-held, and powered by batteries, to allow processing of the samples and amplification reaction in the cartridge at the point of interest. The point of interest may be a field, a grain elevator, a ginning factory etc.

It will be clear that the methods, compositions of matter, kits or devices can be applied to detect nucleic acid sequences of interest, in any biological matter, including biological material derived from any plant, including corn, tobacco, cereal plants including wheat, oat, barley, rye, rice, turfgrass, sorghum, millet or sugarcane plants. The methods of the invention can also be applied to any plant including but not limited to cotton, canola, oilseed rape, soybean, vegetables, potatoes, *Lemna* spp., *Nicotiana* spp., *Arabidopsis*, alfalfa, barley, bean, corn, cotton, flax, pea, rape, rice, rye, safflower, sorghum, soybean, sunflower, tobacco, wheat, asparagus, beet, broccoli, cabbage, carrot, cauliflower, celery, cucumber, eggplant, lettuce, onion, oilseed rape, pepper, potato, pumpkin, radish, spinach, squash, tomato, zucchini, almond, apple, apricot, banana, blackberry, blueberry, cacao, cherry, coconut, cranberry, date, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut and watermelon.

Depending on the biological sample and/or its origin, further optimization of the various parameters of the reaction mixtures described herein may performed, and is well within the reach of the skilled artisan.

It will further be clear that the methods, compositions of matter, kits or devices can also be applied to detect nucleic acid sequences of interest from animals, in biological materials, including from a human, mammal, fish, cattle, goat, pig, sheep, cow, horse, rodent, hamster, mouse, rat, guinea pig, rabbit, primate, nematode, shellfish, prawn, crab, lobster, insect, fruit fly, Coleapteran insect, Dipteran insect, Lepidopteran insect or Homeopteran insect.

The methods, compositions of matter, kits or devices may also be used to detect nucleic acids from lower organisms, including pathogens, such as phytopathogenic fungi or phytopathogenic bacteria or phytopathogenic viruses or animal pathogens, but also e.g. from plant growth promoting bacteria.

It will also be clear that the methods, compositions of matter, kits or devices can be applied to detect any nucleic acid of interest, including transgenes, mutant or variant alleles, marker sequences associated with the presence of a particular trait, such as QTL markers, endogenous sequences, exogenous sequences, viral nucleic acids, pathogen nucleic acids including bacterial or fungal pathogens.

The nucleic acids detected as herein described may be DNA or RNA. To detect RNA, the methods and means described herein may further comprise a reverse transcriptase. The methods and means described herein may also be adapted such that DNA amplification occurs using RNA as template.

Preferably, the amplification reaction is accompanied by a control reaction, i.e. a nucleic acid amplification reaction amplifying a sequence which is known to be present in the nucleic acid extract derived from the biological sample, such as a endogenous sequence. When using a kit or cartridge according to the invention comprising more than one reconstitution and reaction chamber, it is advisable to reserve one reconstitution chamber and one reaction chamber for the control reaction.

The methods, compositions and devices according to the invention may be used to detect nucleic acids characteristic for transgenic events whose characteristic nucleotide sequences can be found in patent applications or regulatory files including Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US2002120964 or WO2002/034946); Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control-herbicide tolerance, deposited as PTA-6233, described in WO2005/103266 or US2005216969); Event 3006-210-23 (cotton, insect control-herbicide tolerance, deposited as PTA-6233, described in US2007143876 or WO2005/103266); Event 3272 (corn, quality trait, deposited as PTA-9972, described in WO2006098952 or US2006230473); Event 40416 (corn, insect control-herbicide tolerance, deposited as ATCC PTA-11508, described in WO2011/075593); Event 43A47 (corn, insect control-herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US2006162007 or WO2004053062); Event B16 (corn, herbicide tolerance, not deposited, described in US2003126634); Event BPS-CV127-9 (soybean, herbicide tolerance, deposited as NCIMB No. 41603, described in WO2010/080829); Event CE43-67B (cotton, insect control, deposited as DSM ACC2724, described in US2009217423 or WO2006/128573); Event CE44-69D (cotton, insect control, not deposited, described in US20100024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US2006130175 or WO2004039986); Event COT202 (cotton, insect control, not deposited, described in US2007067868 or WO2005054479); Event COT203 (cotton, insect control, not deposited, described in WO2005/054480); Event DAS40278 (corn, herbicide tolerance, deposited as ATCC PTA-10244, described in WO2011/022469); Event DAS-59122-7 (corn, insect control-herbicide tolerance, deposited as ATCC PTA 11384, described in US2006070139); Event DAS-59132 (corn, insect control-herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US2009137395 or WO2008/112019); Event DP-305423-1 (soybean, quality trait, not deposited, described in US2008312082 or WO2008/054747); Event DP-32138-1 (corn, hybridization system, deposited as ATCC PTA-9158, described in US20090210970 or WO2009/103049); Event DP-356043-5 (soybean, herbicide tolerance, deposited as ATCC PTA-8287, described in US20100184079 or WO2008/002872); Event EE-1 (brinjal, insect control, not deposited, described in WO2007/091277); Event FI117 (corn, herbicide tolerance, deposited as ATCC 209031, described in US2006059581 or WO1998/044140); Event GA21 (corn, herbicide tolerance, deposited as ATCC 209033, described in US2005086719 or WO1998/044140); Event GG25 (corn, herbicide tolerance, deposited as ATCC 209032, described in US2005188434 or WO1998/044140); Event GHB119 (cotton, insect control-herbicide tolerance, deposited as ATCC PTA-8398, described in WO2008/151780); Event GHB614 (cotton, herbicide tolerance, deposited as ATCC PTA-6878, described in US2010050282 or WO2007/017186); Event GJ11 (corn, herbicide tolerance, deposited as ATCC 209030, described in US2005188434 or WO1998/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US2004172669 or WO2004/074492); Event JOPLIN1 (wheat, disease tolerance, not deposited, described in US2008064032); Event LL27 (soybean, herbicide tolerance, deposited as NCIMB41658, described in WO2006/108674 or US2008320616); Event LL55 (soybean, herbicide tolerance, deposited as NCIMB 41660, described in WO2006/108675 or US2008196127); Event LLcotton25 (cotton, herbicide tolerance, deposited as ATCC PTA-3343, described in WO2003013224 or US2003097687); Event LLRICE06 (rice, herbicide tolerance, deposited as ATCC-23352, described in U.S. Pat. No. 6,468,747 or WO2000/026345); Event LLRICE601 (rice, herbicide tolerance, deposited as ATCC PTA-2600, described in US20082289060 or WO2000/026356); Event LY038 (corn, quality trait, deposited as ATCC PTA-5623, described in US2007028322 or WO2005061720); Event MIR162 (corn, insect control, deposited as PTA-8166, described in US2009300784 or WO2007/142840); Event MIR604 (corn, insect control, not deposited, described in US2008167456 or WO2005103301); Event MON15985 (cotton, insect control, deposited as ATCC PTA-2516, described in US2004-250317 or WO2002/100163); Event MON810 (corn, insect control, not deposited, described in US2002102582); Event MON863 (corn, insect control, deposited as ATCC PTA-2605, described in WO2004/011601 or US2006095986); Event MON87427 (corn, pollination control, deposited as ATCC PTA-7899, described in WO2011/062904); Event MON87460 (corn, stress tolerance, deposited as ATCC PTA-8910, described in WO2009/111263 or US20110138504); Event MON87701 (soybean, insect control, deposited as ATCC PTA-8194, described in US2009130071 or WO2009/064652); Event MON87705 (soybean, quality trait-herbicide tolerance, deposited as ATCC PTA-9241, described in US20100080887 or WO2010/037016); Event MON87708 (soybean, herbicide tolerance, deposited as ATCC PTA9670, described in WO2011/034704); Event MON87754 (soybean, quality trait, deposited as ATCC PTA-9385, described in WO2010/024976); Event MON87769 (soybean, quality trait, deposited as ATCC PTA-8911, described in US20110067141 or WO2009/102873); Event MON88017 (corn, insect control-herbicide tolerance, deposited as ATCC PTA-5582, described in US2008028482 or WO2005/059103); Event MON88913 (cotton, herbicide tolerance, deposited as ATCC PTA-4854, described in WO2004/072235 or US2006059590); Event MON89034 (corn, insect control, deposited as ATCC PTA-7455, described in WO2007/140256 or US2008260932); Event MON89788 (soybean, herbicide tolerance, deposited as ATCC PTA-6708, described in US2006282915 or WO2006/130436); Event MS11 (oilseed rape, pollination control-herbicide tolerance, deposited as ATCC PTA-850 or PTA-2485, described in WO2001/031042); Event MS8, (oilseed rape, pollination control-herbicide tolerance, deposited as ATCC PTA-730, described in WO2001/041558 or US2003188347); Event NK603 (corn, herbicide tolerance, deposited as ATCC PTA-2478, described in US2007-292854); Event PE-7 (rice, insect control, not deposited, described in WO2008/114282); Event RF3, (oilseed rape, pollination control-herbicide tolerance, deposited as ATCC PTA-730, described in WO2001/041558 or US2003188347); Event RT73 (oilseed rape, herbicide tolerance, not deposited, described in WO2002/036831 or US2008070260); Event T227-1 (sugar beet, herbicide tolerance, not deposited, described in WO2002/44407 or US2009265817); Event T25 (corn, herbicide tolerance, not deposited, described in US2001029014 or WO2001/051654); Event T304-40 (cotton, insect control-herbicide tolerance, deposited as ATCC PTA-8171, described in US2010077501 or WO2008/122406); Event T342-142 (cotton, insect control, not deposited, described in WO2006/128568); Event TC1507 (corn, insect control-herbicide tolerance, not deposited, described in US2005039226 or WO2004/099447); Event VIP1034 (corn, insect control-herbicide tolerance, deposited as ATCC PTA-3925, described in WO2003/052073), Event 32316 (corn, insect control-herbicide tolerance, deposited as PTA-11507, described in WO2011/153186A1), Event 4114 (corn, insect control-herbicide tolerance, deposited as PTA-11506, described in WO2011/084621), event EE-GM3/FG72 (soybean, herbicide tolerance, deposited as ATCC Accession No PTA-11041 described in WO2011/063413A2), event DAS-68416-4 (soybean, herbicide tolerance, deposited as ATCC Accession No PTA-10442, WO2011/066360A1), event DAS-68416-4 (soybean, herbicide tolerance, deposited as ATCC Accession No PTA-10442, WO2011/066384A1), event DP-040416-8 (corn, insect control, deposited as ATCC Accession No PTA-11508, WO2011/075593A1), event DP-043A47-3 (corn, insect control, deposited as ATCC Accession No PTA-11509, WO2011/075595A1), event DP-004114-3 (corn, insect control, deposited as ATCC Accession No PTA-11506, WO2011/084621A1), event DP-032316-8 (corn, insect control, deposited as ATCC Accession No PTA-11507, WO2011/084632A1), event MON-88302-9 (oilseed rape, herbicide tolerance, deposited as ATCC Accession No PTA-10955, WO2011/153186A1), event DAS-21606-3 (soybean, herbicide tolerance, deposited as ATCC Accession No. PTA-11028, WO2012/033794A2), event MON-87712-4 (soybean, quality trait, deposited as ATCC Accession No. PTA-10296, WO2012/051199A2), event DAS-44406-6 (soybean, stacked herbicide tolerance, ATCC Accession No. PTA-11336, WO2012/075426A1), event DAS-14536-7 (soybean, stacked herbicide tolerance, deposited as ATCC Accession No. PTA-11335, WO2012/075429A1), event SYN-000H2-5 (soybean, herbicide tolerance, deposited as ATCC Accession No. PTA-11226, WO2012/082548A2), event DP-061061-7 (oilseed rape, herbicide tolerance, no deposit No available, WO2012071039A1), event DP-073496-4 (oilseed rape, herbicide tolerance, no deposit No available, US2012131692), event 8264.44.06.1 (soybean, stacked herbicide tolerance, deposited as Accession No PTA-11336, WO2012075426A2), event 8291.45.36.2 (soybean, stacked herbicide tolerance, Accession No. PTA-11335, WO2012075429A2) (all patent applications hereby incorporated by reference).

The following non-limiting Examples describe the optimization of the amplification reaction to allow direct use of the alkaline extract containing the nucleic acid of biological samples without prior dilution or neutralization.

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR-Basics: From Background to Bench, First Edition, Springer Verlag, Germany.

The sequence listing contained in the file named "BCS12-2016_ST25.txt", which is 2 kilobytes (size as measured in Microsoft Windows®), contains 6 sequences SEQ ID NO: 1 through SEQ ID NO: 6 is filed herewith by electronic submission and is incorporated by reference herein.

In the description and examples, reference is made to the following sequences:
SEQ ID No 1: F3 oligonucleotide primer
SEQ ID No 2: B3 oligonucleotide primer
SEQ ID No 3: FIP oligonucleotide primer
SEQ ID No 4: BIP oligonucleotide primer
SEQ ID No 5: LoopF oligonucleotide primer
SEQ ID No 6: LoopR oligonucleotide primer The above description of the invention is intended to be illustrative and not limiting. Various changes or modifications in the embodiments described may occur to those skilled in the art. These can be made without departing from the spirit or scope of the invention.

EXAMPLES

Example 1: Conditions for DNA Extraction

For nucleic acid or DNA extracts from biological samples, a solution of 50 mM KOH and 1 ng/µl fish sperm DNA (Roche) was used. By using 50 mM KOH (0,28%) as extraction solution we can omit the presence of KCl in the reaction buffer and therefore keep the overall ionic strength low. The DNA concentration in crude extracts is very low. To prevent unspecific binding of the DNA to the tubes we use carrier DNA. In addition the carrier DNA prevents amplification of unspecific products in NTCs (no template controls).

A leaf disc from cotton, soybean or canola was taken by closing an Eppendorf reaction tube over a leaf 0,5 ml of the above extraction buffer is added. The leaf is incubated 8 min at 65° C. without any mechanical treatment or punched 10 times with the tip of a 0,5 ml pipette and incubated 5 min at room temperature. 20 µl of the crude DNA extract is added directly to the lyophilized mastermix for LAMP reaction (see Example 2) and the samples are incubated in a real time PCR machine at 65° C.

To 100 mg of seed powder from cotton, soybean or Canola 40 ml of extraction solution was added in a 50 ml reaction tube. The seed powder was suspended and the sample incubated 5 min at room temperature. An aliquot of 20 µl of the supernatant was used for the reactions.

Example 2: LAMP Reaction Conditions

LAMP primers were designed using the LAMP Designer software (Premier Biosoft International) and suitable primers were synthesized.

A mastermix is prepared containing the following components:
a. 30 mM Ammoniumpentaborate (Sigma)
b. 40 mM malic acid (Sigma)
c. 0,8 M Betaine (5 M solution for PCR from Sigma)
d. 5% Trehalose (Sigma)
e. 8 mM $Mg_2SO_4$ (Sigma)
f. 0,8 mM dNTPs (Promega)
g. 0,2 µM F3 primer
h. 0,2 µM B3 primer
i. 1,5 µM FIP primer
j. 1,5 µM BIP primer
k. 0,75 µM LoopF primer
l. 0,75 µM LoopB primer
m. 0,4 U/µl Polymerase GspSSD (Optigene)
n. 0,0004 U/µl Pyrophosphatase ApePPiase (Optigene)
o. 0.8× fluorescent dye EvaGreeen® from a 20× commercially available stock solution Aliquots of 20 µl were deposited in small reaction tubes or 96 well plates and lyophilized two hours at 0,77 mbar in a Christ Delta 1-24 LSC lyophilizer.

20 µl of DNA in extraction solution (see Example 1) was directly added to one well with lyophilized mastermix and the samples were incubated in a real time PCR machine at 65° C.

Figure 3:
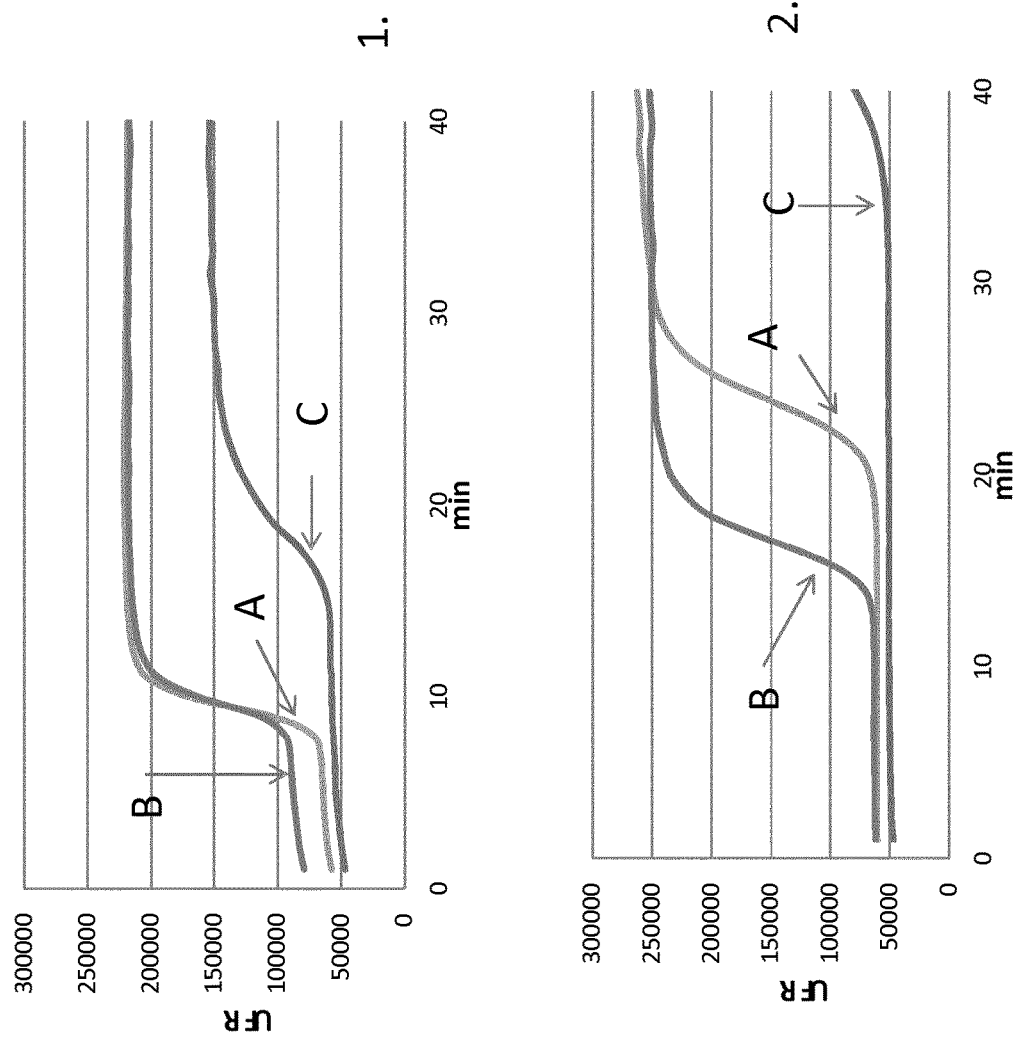
FIG. 3: Comparison of different reaction conditions for LAMP reaction. Panel 1. amplification of catalase; Panel 2. amplification of double mutated epsps. A: buffer conditions A; B: buffer conditions; C: buffer conditions (see Example 1).

Example 3: Comparison of Prior Art Buffers and Buffers According to the Invention for LAMP Reactions 100 mg of soybean seed powder (containing a transgenic 2mEPSPS gene) was extracted with 40 ml extraction solution (50 mM KOH, 1 ng/µl fish sperm DNA) for 5 min at room temperature. 20 µl of the extract was added to the lyophilized mastermixes with the following compositions:
Buffer A:
a. 100 mM Ammoniumpentaborate
b. 10 mM malic acid
c. 1% Trehalose
d. 0,8 M betaine
e. 6 mM $Mg_2SO_4$
f. 0,4 mM dNTPs
g. 0,8× EvaGreen®
h. 1× primermix
i. 0,4 U GspSSD/µl
Buffer B:
a. 30 mM Ammoniumpentaborate
b. 40 mM malic acid
c. 5% Trehalose
d. 0,8 M betaine
e. 6 mM $Mg_2SO_4$
f. 0,4 mM dNTPs
g. 0,8× EvaGreen®
h. 1× primermix
i. 0,4 U GspSSD/µl
Buffer C:
a. Optigene® 10× buffer
b. 50 mM Tris-HCl pH 8,1
c. 30 mM KCl
d. 30 mM $(NH_4)_2SO_4$
e. 0,1% Triton X-100
f. 5% Trehalose
g. 0,8 M betaine
h. 6 mM $Mg_2SO_4$
i. 0,4 mM dNTPs
j. 0,8× EvaGreen®
k. 1× primermix
l. 0,4 U GspSSD/µl The samples were incubated in a real time PCR machine at 65° C. The results are represented in FIG. 3. Panel 1: detection of the catalase amplicon. Panel 2: detection of the 2mepsps amplicon.

Amplification of transgenic 2mEPSPS works best with the Ammoniumpentaborate buffer B. Results may further depend on the plant species. For oilseed rape samples, buffer A with higher ammoniumpentaborate concentrations may be better. However, buffer B appears a suitable buffer over different biological samples.

Example 4: Detection of Catalase in Cotton Leaves Using Cartridge

In milled cartridge prototypes, leaves from soy or cotton were sampled by a punching mechanism, which in the same turn closed and sealed the cartridge. The DNA extraction solution, present in a coated aluminium blister, was forced over the leaf punch by machine-controlled squeezing of the blister. This crude DNA-containing extract was guided through a filter pad, containing the lyophilized LAMP reagents. The extract reconstituted the biochemicals and reached the reaction chamber. The reaction mixture was heated to 65° C., starting the LAMP-based DNA amplification. A fluorescent intercalating dye present in the mixture was excited by blue light and the resulting fluorescence detected and quantified by an external instrument.

Plant leaf samples are being extracted with 50 mM KOH, 1 ng/μl fish sperm carrier DNA (Roche). Prototype cartridges were milled from POM polymer blocks. The extraction fluid was filled into single-use aluminium blisters coated with polypropylene. The reaction buffer was lyophilized onto polypropylene pads. The cartridge was actuated using a lab setup consisting of a linear motor for blister pressing, a heating unit (65° C.), a LED (468 nm) for fluorescent excitation and a camera for imaging purposes.

LAMP reactions for catalase from cotton were performed using the following primers: 0,2 μM F3 (GATAAGTTGCTCCAGACTCG; SEQ ID No 1), 0,2 μM B3 (GCATGACGAACAGGATCGTACC; SEQ ID No 2), 15 μM FIP (ATTGGCTGGGAGTTGCAGATAGTTATTCTCCTACTCTGATACCCA; SEQ ID No 3), 15 μM BIP (GCTCCC AAGTGTGCTCATCAATCTCCTCATCCCTGTGC; SEQ ID No 4), 8 μM LoopF (AGTTTGGCCCAAGTCTGT GCCT; SEQ ID No 5), 8 μM LoopR (CAATCACCACGAAGG TTTTATG; SEQ ID No 6). Reaction buffer consisted of 30 mM Ammoniumpentaborate, 40 mM malic acid, 0,8M betaine, 5% trehalose, 8 mM $Mg_2SO_4$, 0,8 mM dNTPs, 0,8× Evagreen[4] (Biotium, Hayward, USA), 0,4 U/μl GspSSD (Optigene, UK) and pyrophosphatase, 0.0004 U/μl.

The results of the amplification in the presence and absence of the DNA of interest are represented in FIG. 4C.

Figure 4:
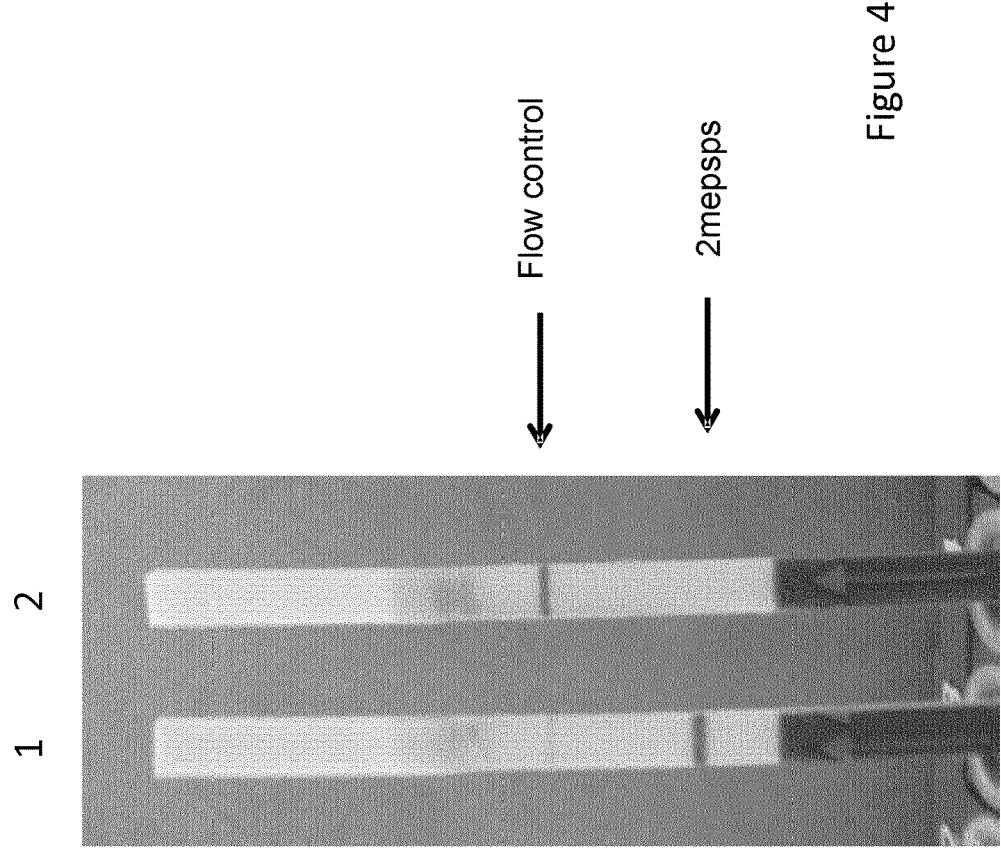
FIG. 4: Lateral Flow Strip detection of LAMP products. LAMP was performed with Biotin and FAM labeled loop primers and detected on HybriDetect strips from Milenia Biotec. Lane 1: Cotton GHB614 (containing double mutated EPSPS gene); Lane 2: wild-type cotton.

Example 5: Alternative Detection by Lateral Flow Strip Detection after LAMP Reaction LAMP was performed with Biotin and FAM labelled loop primers on biological samples of cotton comprising transgenic event GHB614 (comprising a 2mEPSPS coding region) and wildtype cotton as a negative control and detected on HybriDetect strips from Milenia Biotec. The results are represented in FIG. 4.

Example 6: Optimization of LAMP Reaction Conditions after Alkaline DNA Extraction The influence of different concentrations of constituents of the reaction mixture for nucleic acid amplification by LAMP were tested. DNA extracts obtained in accordance with Example 1 were tested under various concentrations of organic acid, detergent or ammoniumpentaborate. A set of three samples in four replicates was tested for each certain reaction condition.

Amplification with crude DNA extractions show a higher variation compared to amplifications on purified DNA which may be due to the presence of some particles in the solution.

Figure 5:
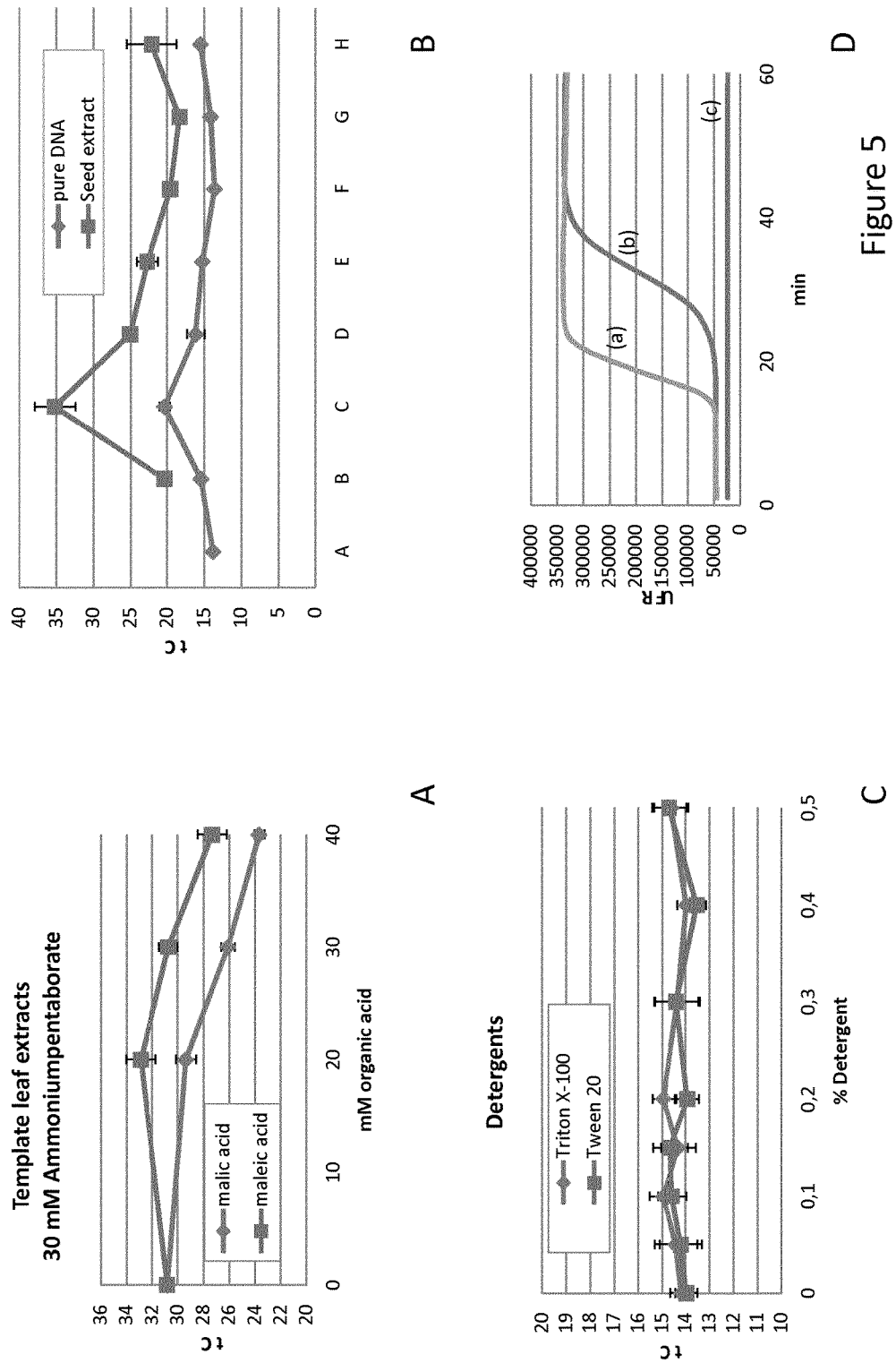
FIG. 5: Panel A: influence of the type of organic acid and concentration on LAMP reaction. Panel B: Influence of different concentrations of ammoniumpentaborate on the LAMP reaction. Panel C: Influence of detergents on the LAMP reaction. Panel D: Comparison of the presence and absence of maleic acid or citric acid on the LAMP reaction (a) with 40 mM maleic acid; (b) without organic acid; (c) with 40 mM citric acid.

In one experiment the influence of the type of additional organic acid on the LAMP reaction was tested. DNA was extracted from cotton leaf and the target nucleic acid was catalase. The results (FIG. 5A) indicate that malic acid results in quicker amplification than maleic acid.

In another experiment the influence of the type of additional organic acid on the LAMP reaction was tested. DNA was extracted from cotton leaf and the target nucleic acid was catalase. The results (FIG. 5D) indicate that maleic acid results in quicker amplication than in the absence of maleic acid, while citric acid appear to have an inhibitory effect.

In a further experiment the influence of the concentration of ammoniumpentaborate and of malic acid on the LAMP reaction was tested. DNA was extracted from cotton leaf or cotton seed and the target nucleic acid was 2mEPSPS. The results (FIG. 5B) indicate that optimal conditions, for cotton leaf extracts appear to be A or F as set forth in the below table.

|   | Ammoniumpentaborate (mM) | Malic acid (mM) |
|---|---|---|
| A | 40 | 40 |
| B | 55 | 40 |
| C | 70 | 40 |
| D | 96 | 40 |
| E | 96 | 30 |
| F | 96 | 20 |
| G | 96 | 10 |
| H | 96 | 0 |

In yet a further experiment the influence of the concentration and type of detergent was investigated. DNA was extracted from cotton leaf and the target nucleic acid was catalase. The results (FIG. 4C) indicate that there is little difference between detergents, nor that the concentration played a critical role. The inclusion of detergents appears to have a positive influence on the incidence of positive no template controls.

In conclusion, the current invention is directed at least to the composition of matter, kits, methods and uses as described in the following paragraphs:

1. A composition of matter comprising a mixture of deoxynucleotides (dNTPs), divalent cations, an enzyme capable of DNA amplification, and primers suitable to amplify a nucleic acid of interest or a DNA of interest characterized in that said the mixture has a buffering capacity at a sufficiently low ionic strength to sufficiently neutralize an alkaline solution containing template nucleic acid or DNA in order to allow the amplification enzyme to function.
2. The composition of matter according to paragraph 1, wherein the mixture comprises a salt containing ammonium as cation and an anion of a weak acid, and/or an organic acid, preferably a dicarboxylic acid.
3. The composition of matter according to paragraph 2, wherein said salt is ammoniumpentaborate.
4. The composition of paragraph 2 or 3, wherein the organic acid is malic acid.

5. The composition of paragraph 2, wherein the organic acid is selected from oxalic acid, malonic acid, succinic acid, glutaric acid, adipic acid, pimelic acid, suberic acid, azelaic acid, sebacic acid, glucuronic acid, lactic acid, tartaric acid, fumaric acid, maleic acid or a mixture thereof.

6. The composition of any one of paragraphs 2 to 5, wherein the ammoniumpentaborate has a final concentration of between 10 mM and 100 mM, preferably between 30 mM and 40 mM.

7. The composition of matter of paragraph 6, wherein the ammoniumpentaborate has a final concentration of 30 mM.

8. The composition of any one of paragraphs 2 to 4 or 6 to 7, wherein the malic acid has a final concentration of between 10 mM and 40 mM, preferably 40 mM.

9. The composition of matter of any one of paragraphs 1 to 8, wherein the divalent cations are provided by $Mg_2SO_4$ (or other magnesium salts) which has a final concentration of between 1-10 mM, preferably between 4-8 mM.

10. The composition of matter of any one of paragraphs 1 to 9, wherein the dNTPS have a final concentration of between 0,2 mM to 1,4 mM, preferably 0.4 mM to 0.9 mM.

11. The composition of any one of paragraphs 1 to 10, wherein the enzyme capable of DNA amplification is selected from DNA I polymerase, Klenow polymerase, TaqI polymerase, a DNA polymerase with strand displacing properties, phi 29 polymerase, Bst polymerase, Csa polymerase, 96-7 polymerase, Bsm polymerase, GspSSD polymerase.

12. The composition of any one of paragraphs 1 to 11, further comprising molecules allowing fluorescent detection of amplified nucleic acid or DNA.

13. The composition of paragraph 12, wherein the molecules are dimeric dyes comprising monomeric dyes linked by a neutral molecule, which become fluorescent only when bound to nucleic acid.

14. The composition of paragraph 12, wherein the molecules are intercalating dyes.

15. The composition of paragraph 12, wherein the molecules are N',N'-dimethyl-N-[4-[(E)-(3-methyl-1,3-benzothiazol-2-ylidene)methyl]-1-phenylquinolin-1-ium-2-yl]-N-propylpropane-1,3-diamine)

16. The composition of any one of paragraphs 1 to 11, further comprising molecules allowing detection of amplified nucleic acid via antibody specific binding or affinity binding, or via a hybridization-based assay.

17. The composition of any one of paragraphs 1 to 16, further comprising a detergent, such as Triton X-100, preferably in a concentration of between 0.01% and 0.5%, preferably about 0.1%, or Tween 20, or Pluronic F-69 or mixtures thereof.

18. The composition of any one of paragraphs 1 to 17, further comprising a lyophilization protection agent, preferably trehalose, preferably in a final concentration of about 5%.

19. The composition of any one of paragraphs 1 to 18, further comprising betaine in a concentration of between 0.05 mM to 1 M.

20. The composition of any one of paragraphs 1 to 19, further comprising primers suitable to amplify a nucleic acid or interest or a DNA sequence of interest in a plant of interest.

21. The composition of paragraph 20, wherein said nucleic acid or DNA sequence of interest is specific for a commercially available transformation event.

22. The composition of paragraph 20, wherein said nucleic acid or DNA sequence of interest is specific for a experimentally available transformation event.

23. The composition of paragraph 20, wherein said nucleic acid or DNA sequence of interest is specific for the presence of a specific allele, such as a variant allele.

24. The composition of paragraph 20, wherein said nucleic acid or DNA sequence is a marker, such as a QTL marker.

25. The composition of any one of paragraphs 1 to 24, wherein the final concentration of the primers is between 0,2 µM and 75 µM.

26. The composition of any one of paragraphs 1 to 25, which has been lyophilized.

27. The composition of any one of paragraphs 1 to 26, which further comprises a template nucleic acid or DNA.

28. The composition of paragraph 26, which has been solubilized with an alkaline solution comprising template nucleic acids or DNA.

29. The composition of paragraph 26, which has been solubilized with an alkaline solution comprising template nucleic acid or DNA and carrier DNA.

30. The composition of any one of paragraphs 1 to 26 to which template nucleic acid or DNA has been added in an alkaline solution.

31. A kit comprising the composition of matter of any one of paragraphs 1 to 26.

32. The kit of paragraph 31, comprised within a device, said device comprising
   a. a means for sampling of the biological material;
   b. a liquid reservoir comprising an alkaline extraction solution;
   c. appropriate channels to direct the alkaline extraction solution, upon activation, over the biological sample into the reaction mixture; and
   d. optionally a means to detect amplification of nucleic acids.

33. The kit of paragraph 31, comprised within a cartridge, said cartridge comprising
   a) a first component, preferably abase component, preferably covered on both sides with transparent coats, thereby forming channels and chambers (1) and a second component, preferably a cover component (2), fitting together to be closed, preferably by aligning one structure onto the other, preferably around a hinge section (3);
   b) said first and second or said base and cover components containing fitting and corresponding chamber parts (4) and (5) which when the first and second component or base and cover component are aligned form a chamber A, fit to receive the biological sample; wherein the chamber A is preferably watertight;
   c) said first or said base component further comprising attached to it, a liquid reservoir (9) containing an alkaline solution; said liquid reservoir being connected to chamber A via a channel (10);
   d) said first or said base component further containing at least one, preferably two chambers B (11) (12) connected to said chamber A or said base chamber A part (4) by at least one channel (13);

e) said first or said base component further containing at least one, preferably two chambers C (15) (16), each connected to said at least one chamber B by a channel (17) (18);
f) said first component or said base component, further optionally containing at least one, preferably two chambers D (19)(20), each connected to said at least one chamber C by a channel (21) (22);
g) said second component or said cover component preferably containing a physical access (23), preferably a hole, to allow interaction with the liquid reservoir (9);
h) said second or cover component further optionally containing at least one, preferably two optically transparent region(s) over the region of said chamber B or said two chambers C allowing monitoring of the chamber B or C (24) (25);
wherein said composition of matter is contained within said chambers B.

34. A kit according to any one of paragraphs 31 to 33 comprising a device for affinity-based or antibody-based or hybridization-based detection of amplified nucleic acid, such as a lateral flow strip.

35. A method for amplifying a nucleic acid or interest or a DNA of interest comprising using a composition of any one of paragraphs 1 to 26 or a kit of paragraphs 31 to 34.

36. The method of paragraph 35, characterized in that the amplification of DNA is an isothermal amplification process.

37. The method of any one of paragraphs 35 or 36 wherein the template nucleic acid or DNA is provided in an alkaline solution.

38. The method of any one of paragraphs 35 to 37 wherein the template nucleic acid or DNA in the alkaline solution, further comprises carrier DNA.

39. The method of any one of paragraphs 35 to 38 wherein the amplified DNA is specifically detected via fluorescence detection.

40. The method of any one of paragraphs 35 to 38 wherein the amplified DNA is specifically detected via specific antibody recognition or affinity binding based detection or hybridization based detection or a combination thereof.

41. A method for amplification of nucleic acid or interest or DNA of interest, comprising the steps of
    a. isolating template nucleic acid or DNA from a biological sample using an alkaline extraction solution
    b. providing ingredients and conditions to amplify DNA
    wherein said isolated template nucleic acid or DNA in said alkaline extraction solution is not diluted or not neutralized prior to said step b).

42. The method of paragraph 41, wherein the alkaline extraction solution contains KOH, NaOH or LiOH.

43. The method of paragraph 41, wherein the alkaline extraction solution contains KOH, preferably in a concentration of 25 mM to 100 mM, particularly in a concentration of about 50 mM.

44. The method of paragraph 41, wherein said ingredients comprise a composition according to any one of paragraphs 1 to 25.

45. The method of paragraph 41 to 43, wherein said biological sample is a plant part, organ or tissue.

46. The method of paragraph 41 to 43, wherein said biological sample is a portion of a plant leaf.

47. The method of any one of paragraphs 41 to 45 wherein said biological sample is processed without further mechanical maceration.

48. The method of any one of paragraphs 41 to 46, wherein said biological sample comprises seed, preferably seed powder.

49. The method of any one of paragraphs 41 to 46, wherein said biological sample comprises single seeds.

50. The method of any one of paragraphs 41 to 46, wherein said biological sample comprises seed chips.

The invention claimed is:

1. A composition comprising:
   (a) a mixture of deoxynucleotides (dNTPs), divalent cations, a DNA-amplification enzyme, and amplification primers; and
   (b) a buffer comprising (i) a salt of ammonium and an anion of a weak acid and (ii) a dicarboxylic acid, wherein said buffer has a buffering capacity at a sufficiently low ionic strength to sufficiently neutralize an alkaline solution comprising template nucleic acid or DNA in order to allow the amplification enzyme to function, wherein said salt is ammonium pentaborate, and wherein the dicarboxylic acid is malic acid, or the dicarboxylic acid is oxalic acid, malonic acid, succinic acid, glutaric acid, adipic acid, pimelic acid, suberic acid, azelaic acid, sebacic acid, tartaric acid, fumaric acid, maleic acid or a mixture thereof.

2. A kit comprising the composition of claim 1.

3. A device comprising a kit according to claim 2, said device further comprising
   a) a chamber for sampling of plant material;
   b) a liquid reservoir comprising an alkaline extraction solution; and
   c) channels to direct the alkaline extraction solution, upon activation, over the plant material into the mixture.

4. A cartridge comprising the kit of claim 2, said cartridge further comprising
   a) a first component, and a second component, fitting together to be closed;
   b) said first and second components comprising fitting and corresponding chamber parts which, when the first and second component are aligned, form a chamber A, fit to receive a biological sample;
   c) said first component further comprising, attached to it, a liquid reservoir comprising an alkaline solution; said liquid reservoir being connected to said chamber A via a channel;
   d) said first component further comprising at least one chamber B connected to said chamber A by at least one channel;
   e) said first component further comprising at least one chamber C connected to said at least one chamber B by at least one channel; and
   f) said second component comprising a physical access to allow interaction with the liquid reservoir;
   wherein said composition is contained within at least one said chamber B.

5. A method for amplifying a nucleic acid of interest or a DNA of interest comprising applying the composition of claim 1 to nucleic acid of interest or DNA of interest.

6. The method of claim 5, wherein the amplification of DNA is an isothermal amplification process.

7. The method of claim 5, wherein the template nucleic acid or DNA is included in an alkaline solution.

8. The method of claim 7, wherein the template nucleic acid or DNA in the alkaline solution further comprises carrier DNA.

9. A method for amplification of a nucleic acid of interest or DNA of interest, comprising
   a. isolating template nucleic acid or DNA from a plant sample using an alkaline extraction solution; and
   b. amplifying said nucleic acid or DNA using the composition according to claim 1 wherein said isolated template nucleic acid or DNA in said alkaline extraction solution is not diluted or not neutralized prior to said step b) application.

10. The method of claim 9, wherein the alkaline extraction solution comprises KOH, NaOH or LiOH or mixtures thereof.

11. The method of claim 9, wherein said plant sample is a plant part, organ or tissue, a plant leaf, seed, seed powder, single seeds or seed chips.

12. The device of claim 3, wherein said device is capable of detecting amplification of nucleic acids.

13. The cartridge of claim 4, wherein the first component is a base component and wherein the second component is a cover component.

14. A method for amplifying a nucleic acid of interest or a DNA of interest comprising using the kit of claim 2.

15. A method for amplifying a nucleic acid of interest or a DNA of interest comprising using the device of claim 3.

16. A method for amplifying a nucleic acid of interest or a DNA of interest comprising using the cartridge of claim 4.

17. The method of claim 9, wherein said salt is ammonium pentaborate.

18. The method of claim 9, wherein said alkaline extraction solution comprises KOH in a concentration of 25 mM to 100 mM.

19. The method of claim 9, wherein said biological sample is processed without further mechanical maceration.

20. The composition of claim 1, wherein the DNA-amplification enzyme is DNA I polymerase, Klenow polymerase, TaqI polymerase, a DNA polymerase with strand displacing properties, phi 29 polymerase, Bst polymerase, Csa polymerase, 96-7 polymerase, Bsm polymerase, or GspSSD polymerase.

21. The composition of claim 1, wherein the composition is suitable for use with an isothermal amplification process.

22. The composition of claim 1, wherein the composition is suitable for use with Loop-mediated Isothermal Amplification (LAMP), Recombinase Polymerase Amplification (RPA), Polymerase chain Reaction (PCR), or Nicking Enzyme Amplification Reaction (NEAR).

23. The composition of claim 1, wherein the composition is suitable for use with LAMP.

24. The method of claim 5, wherein the DNA-amplification enzyme is DNA I polymerase, Klenow polymerase, TaqI polymerase, a DNA polymerase with strand displacing properties, phi 29 polymerase, Bst polymerase, Csa polymerase, 96-7 polymerase, Bsm polymerase, or GspSSD polymerase.

25. The method of claim 5, wherein the method for amplifying is LAMP, RPA, PCR, or NEAR.

26. The method of claim 5, wherein the method for amplifying is LAMP.

27. The method of claim 9, wherein the method for amplification is an isothermal amplification process.

28. The method of claim 9, wherein the DNA-amplification enzyme is DNA I polymerase, Klenow polymerase, TaqI polymerase, a DNA polymerase with strand displacing properties, phi 29 polymerase, Bst polymerase, Csa polymerase, 96-7 polymerase, Bsm polymerase, or GspSSD polymerase.

29. The method of claim 9, wherein the method for amplification is LAMP, RPA, PCR, or NEAR.

30. The method of claim 9, wherein the method for amplification is LAMP.

31. The composition of claim 1, wherein the dicarboxylic acid is malic acid.

32. The method of claim 9, wherein the dicarboxylic acid is malic acid.

* * * * *